(12) United States Patent
Wu et al.

(10) Patent No.: US 10,105,066 B2
(45) Date of Patent: Oct. 23, 2018

(54) METHOD AND APPARATUS FOR CONTROLLING ALARMS

(71) Applicant: Anhui Huami Information Technology Co., Ltd., Hefei, Anhui (CN)

(72) Inventors: Haocheng Wu, Anhui (CN); Hui Wang, Anhui (CN)

(73) Assignee: Anhui Huami Information Technology Co.,Ltd., Hefei, Anhui (CN)

( * ) Notice: Subject to any disclaimer, the term of this patent is extended or adjusted under 35 U.S.C. 154(b) by 0 days.

(21) Appl. No.: 14/994,364

(22) Filed: Jan. 13, 2016

(65) Prior Publication Data

US 2016/0203695 A1    Jul. 14, 2016

(30) Foreign Application Priority Data

Jan. 13, 2015 (CN) .......................... 2015 1 0016608

(51) Int. Cl.
| | | |
|---|---|---|
| G08B 21/06 | (2006.01) | |
| G09B 23/28 | (2006.01) | |
| A61B 5/0205 | (2006.01) | |
| A61B 5/00 | (2006.01) | |

(52) U.S. Cl.
CPC .......... *A61B 5/0205* (2013.01); *A61B 5/4812* (2013.01); *A61B 2503/12* (2013.01)

(58) Field of Classification Search
CPC combination set(s) only.
See application file for complete search history.

(56) References Cited

U.S. PATENT DOCUMENTS

| | | | |
|---|---|---|---|
| 2005/0143617 A1* | 6/2005 | Auphan .................. | A61B 5/08 600/26 |
| 2005/0177051 A1* | 8/2005 | Almen ............... | A61B 5/02405 600/509 |
| 2005/0190065 A1* | 9/2005 | Ronnholm ............ | A61M 21/00 340/575 |
| 2006/0001537 A1* | 1/2006 | Blake ............... | G08B 13/19656 340/521 |

(Continued)

FOREIGN PATENT DOCUMENTS

| | | |
|---|---|---|
| CN | 101997950 A | 3/2011 |
| CN | 103188399 A | 7/2013 |

(Continued)

OTHER PUBLICATIONS

Aschoff, J, Circadian Rhythms in Man, Jun. 11, 1965, American Association for the Advancement of Science, Science, New Series, vol. 148, No. 3676, pp. 1427-1432.*

*Primary Examiner* — Brian Zimmerman
*Assistant Examiner* — Cal Eustaquio
(74) *Attorney, Agent, or Firm* — Young Basile Hanlon & MacFarlane, P.C.

(57) ABSTRACT

Methods, apparatuses and systems for controlling an alarm are set forth herein for reminding a user with assurance of sleep quality. The method includes receiving sleep information, determining a sleep status, determining whether duration of the sleep status reaches a pre-determined duration threshold, and based on a determination that the duration of the sleep status reaches the pre-determined duration threshold, outputting alarming information.

19 Claims, 6 Drawing Sheets

(56) References Cited

U.S. PATENT DOCUMENTS

| | | | |
|---|---|---|---|
| 2006/0183980 A1* | 8/2006 | Yang | A61B 5/6804 600/301 |
| 2007/0049355 A1* | 3/2007 | Wu | G06F 3/0221 455/575.1 |
| 2009/0240155 A1* | 9/2009 | Nakayama | A61B 5/02416 600/500 |
| 2013/0018284 A1 | 1/2013 | Kahn et al. | |
| 2013/0250734 A1* | 9/2013 | Narasani | G04G 13/02 368/9 |
| 2014/0253320 A1* | 9/2014 | Bender | H04M 1/72566 340/521 |
| 2016/0022202 A1* | 1/2016 | Peterson | A61B 5/4812 368/251 |

FOREIGN PATENT DOCUMENTS

| | | |
|---|---|---|
| CN | 103475786 A | 12/2013 |
| CN | 104095615 A | 10/2014 |

\* cited by examiner

METHOD AND APPARATUS FOR CONTROLLING ALARMS

CROSS-REFERENCE TO RELATED APPLICATION

This application claims priority to Chinese patent applications no. CN 201510016608.8, filed on Jan. 13, 2015, which is incorporated herein in its entirety by reference.

TECHNICAL FIELD

The present disclosure generally relates to computer technologies, and more particularly, to methods, apparatuses and systems for controlling alarms.

BACKGROUND

As development of electronic technologies, more and more electronic devices emerge, such as computers, cell phones, tablet computers, as well as "smart" glasses, "smart" wristbands and so on.

Many electronic devices provide a function of alarm clock, which is used almost every day by most users. A user can set up a fixed reminder time, at which an alarm is triggered every day.

However, some users do not want to be waked up at the fixed time, because they care more about sleep quality and do not want to be disturbed by the alarm during when the sleep quality is good. Thus, the reminding method of the alarm should be improved to make the reminder time more consistent with the user requirement and more accurate.

SUMMARY

Disclosed herein are implementations of methods, apparatuses and systems for pushing audio.

In one aspect, the present disclosure includes a method for controlling alarms comprising the steps of receiving sleep information of a user, determining a sleep status based on the received sleep information, determining whether duration of the sleep status reaches a pre-determined duration threshold, and based on a determination that the duration of the sleep status reaches the pre-determined duration threshold, outputting alarming information for triggering a preset action by an alarm.

In another aspect, the present disclosure includes an apparatus for controlling alarms, comprising an acquisition module that receives sleep information of a user, a status module that determines a sleep status based on the received sleep information, a duration determination module that determines whether duration of the sleep status reaches a pre-determined duration threshold, and an output module that outputs alarming information based on a determination that the duration of the sleep status reaches the pre-determined duration threshold.

In another aspect, the present disclosure includes a system for controlling an alarm, comprising a terminal device and a wirelessly connected computing device. The terminal device is configured to transmit a configuration instruction, wherein the configuration instruction comprises a pre-determined duration threshold. The computing device comprises an acquisition module that receives sleep information of a user, a reception module that receives the configuration instruction, a status module that determines a sleep status based on the received sleep information, a date determination module that determines whether a current date associated with the sleep status is a pre-determined holiday, a first determination module that determines a time period of a current time associated with the sleep status, a second determination module that, in accordance with a pre-determined corresponding relation between a time period and a duration threshold, determines the pre-determined duration threshold corresponding to the time period of the current time associated with the sleep status, a duration determination module that determines whether duration of the sleep status reaches the pre-determined duration threshold, and an output module that outputs alarming information based on a determination that the current date is the pre-determined holiday and a determination that the duration of the sleep status reaches the pre-determined duration threshold.

The embodiments or implementations can be configured as executable computer program instructions stored in computer storages such as memory.

BRIEF DESCRIPTION OF THE DRAWINGS

The description here makes reference to the accompanying drawings wherein like reference numerals refer to like parts throughout the several views, and where.

DETAILED DESCRIPTION

Example implementations of the present disclosure will be described below with reference to the accompanying drawings. The same numbers across the drawings set forth in the following description represent the same or similar elements, unless differently expressed. The implementations set forth in the following description do not represent all implementations or embodiments consistent with the present disclosure; on the contrary, they are only examples of apparatuses and methods in accordance with some aspects of this disclosure as detailed in the claims.

With related technologies, many users accustom to be waked up by an alarm every day. The alarm usually goes off at a fixed time. If a user does not want to be waked up at the fixed time, a manual change is needed. If the user forgets to change the fixed time, it is possible that the user will be waked up at an unwanted time, which affects sleep quality of the user.

In implementations of this disclosure, a sleep condition of the user is monitored, and the alarm ring is output when a pre-determined sleep duration is reached. The user is waked up under assurance of sleep quality without performing a manual change to the alarm time, which simplifies the operation for the user.

Figure 1:
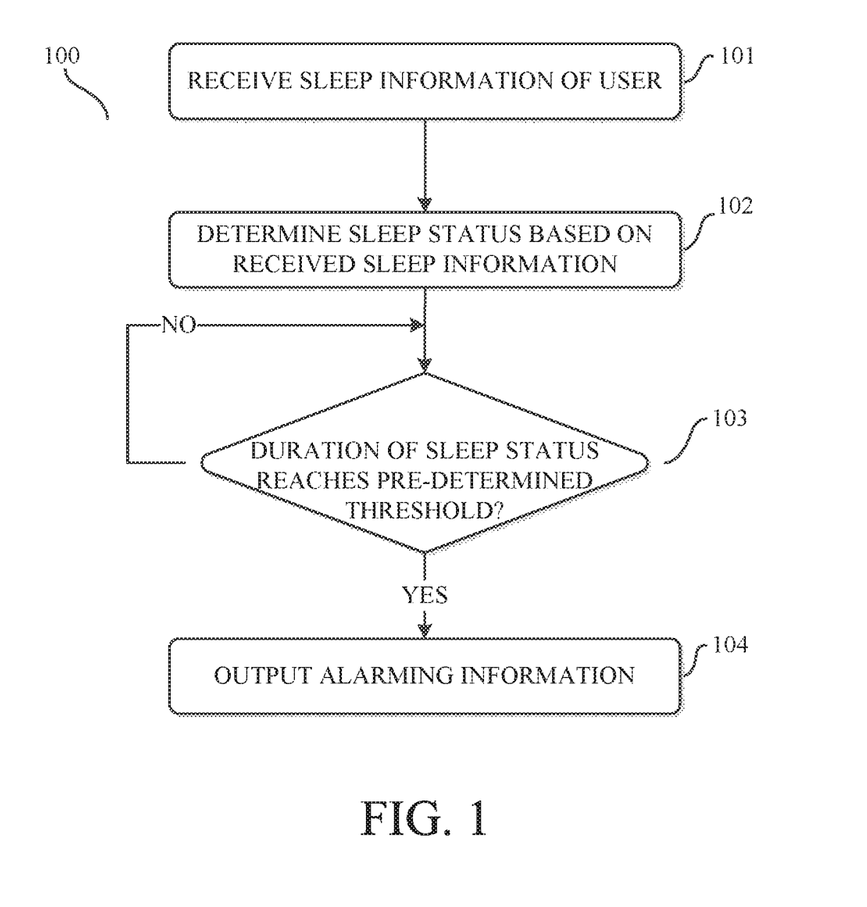
FIG. 1 is a flowchart of a method for controlling an alarm according to implementations of this disclosure.

FIG. 1 is a flowchart of a method for controlling an alarm according to one implementation herein. As shown in FIG. 1, the method can be implemented in a computing device, such as a wearable device, and includes the following operations:

At operation 101, sleep information of the user is received (e.g., received by the computing device such as the wearable device). The act of receiving can include, for example, acquiring, obtaining, identifying, receiving from another device, receiving from the same device as the current device, or otherwise determining information such as data by the computing device.

At operation 102, a sleep status is determined based on the received sleep information.

At operation 103, it is determined whether duration of the sleep status reaches a pre-determined duration threshold. If the duration of the sleep status reaches the pre-determined duration threshold, the process proceeds to operation 104; otherwise, operation 103 is repeated.

At operation 104, alarming information is outputted. The alarming information can include, for example, data for triggering a preset action by an alarm.

In this implementation, the wearable device can monitor the sleep condition of a user, and determine a start time of entering the sleep status based on analysis of the sleep information. Based on a determination that the user is in the sleep status, a timer is started and determines whether the duration of the sleep status reaches the pre-determined duration threshold. If it is found that the user wakes up in the middle of the sleep, the timer stops during when the user is awake. Once the user re-enter the sleep status, the timer continues and determines whether the duration of the sleep status reaches the pre-determined duration threshold. If the duration of the sleep status reaches the pre-determined duration threshold, the alarming information is outputted to wake up the user, which ensures sufficient sleep for the user. For users who do not want to wake up at a fixed time, this implementation provides a better effect.

In some implementations, the wearable device can be a wristband. The user can configure the duration threshold stored in the wristband via a terminal device, such as a cell phone or a mobile terminal, in which the aforementioned method further includes operation A.

At operation A, a configuration instruction transmitted from the terminal device is received, wherein the configuration instruction includes the pre-determined duration threshold.

A connection between the terminal device and the wristband can be established wirelessly, such as Bluetooth, Wi-Fi and so on. An application used for controlling the wristband can be installed in the terminal device. The user input the duration threshold, for example, eight hours, in the application. The terminal device generates a wireless transmission packet, which includes the configuration instruction. For security and identification purpose, the wireless transmission packet can further include an identifier. Then, the terminal device transmits the wireless transmission packet wirelessly to the wristband. The wristband monitors a wireless channel, and parses the wireless transmission packet upon receipt. The wristband authenticates the identifier. Based on a successful authentication, a configuration is made in accordance with the received duration threshold.

During weekdays, the user usually needs to wake up at a fixed time. During holidays, the user usually does not want to wake up at the fixed time. The holidays can include weekends and official holidays such as Memorial Day, Labor Day and Christmas Day. Therefore, the aforementioned method further includes operation B1.

At operation B1, it is determined that whether the current date associated with the sleep status is a pre-determined holiday.

Operation 104 can further include operation B2.

At operation B2, if the current date associated with the sleep status is a pre-determined holiday, and if the duration of the sleep status reaches the pre-determined duration threshold, the alarming information is outputted.

The implementation in weekends and holidays can reduce influence to the user's sleep and ensure sufficient sleep for the user, which provides a better effect.

Besides a normal night sleep, the user can possibly have a habit of siesta. To an aspect of health, the night sleep usually needs to be ensured to be eight hours. However, one hour might be sufficient for the siesta. To accommodate needs for different time periods, before the determining whether the duration of the sleep status reaches the pre-determined duration threshold, the aforementioned method further includes operations C1-C2.

At operation C1, a time period of a current time associated with the sleep status is determined.

At operation C2, in accordance with a pre-determined corresponding relation between a time period and a duration threshold, the pre-determined duration threshold corresponding to the time period of the current time associated with the sleep status is determined.

For example, a time period of 22:00-8:00 can correspond to a duration threshold of eight hours, and a time period of 12:00-14:00 can correspond to a duration threshold of thirty minutes.

In some implementations, the alarming information can include vibration. To avoid disturbing other people, it can be that only the wristband vibrates, and neither the wristband nor the terminal device outputs any ring.

In this disclosure, the wristband can receive the sleep information according to various specific implementations. For example, operation 101 can further include operation D1 and operation D2.

At operation D1, acceleration and/or heart rate information is received.

At operation D2, in accordance with the received acceleration and/or heart rate information, the sleep information is received.

For example, in the case of receiving the sleep information via the acceleration information, if the acceleration within a time period has slight changes with a small frequency of change, it is determined that an activity frequency and an activity amplitude of the user are both small, thus the user is in the sleep status. On the contrary, if the acceleration within a time period has large changes with a large frequency of change, it is determined that the activity frequency and the activity amplitude of the user are both large, thus the user is not in the sleep status.

For another example, in the case of receiving the sleep information via the heart rate information, heart rate information during sleep is pre-determined via statistics, wherein the wristband compares detected heart rate information to the pre-determined heart rate information during sleep for a match. If the match exists, it is determined that the user is in the sleep status; otherwise, it is determined that the user is not in the sleep status.

In the following examples, some implementations of the controlling of an alarm are described with details.

Figure 2:
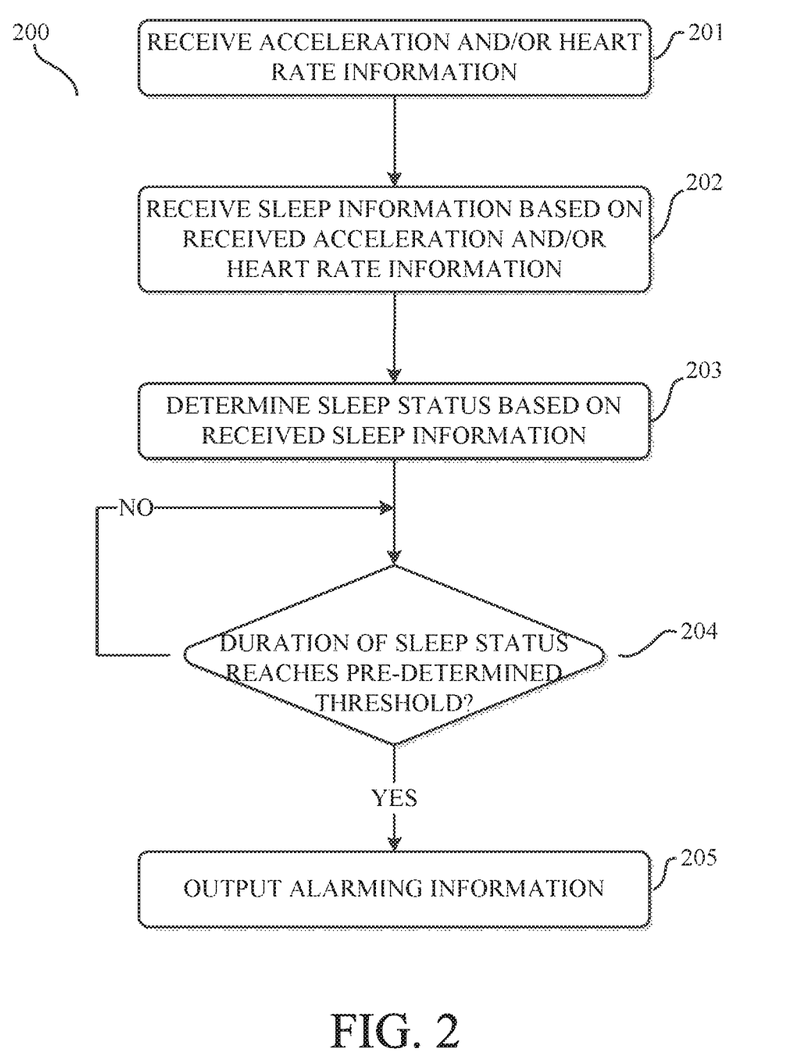
FIG. 2 is a flowchart of another method for controlling an alarm according to implementations of this disclosure.

FIG. 2 is a flowchart of another method for controlling an alarm according to implementations of this disclosure. As shown in FIG. 2, this method can be implemented in a wearable device, including the following operations.

When the current date associated with the sleep status is a pre-determined holiday, this implementation can be adopted.

At operation 201, acceleration and/or heart rate information is received.

At operation 202, in accordance with the received acceleration and/or heart rate information, the sleep information is received.

At operation 203, in accordance with the received sleep information, a sleep status is determined.

At operation 204, it is determined whether duration of the sleep status reaches a pre-determined duration threshold. If the duration of the sleep status reaches the pre-determined duration threshold, the process proceeds to operation 205; otherwise, if the duration of the sleep status does not reach the pre-determined duration threshold, operation 204 is repeated.

At operation 205, alarming information is outputted.

Figure 3:
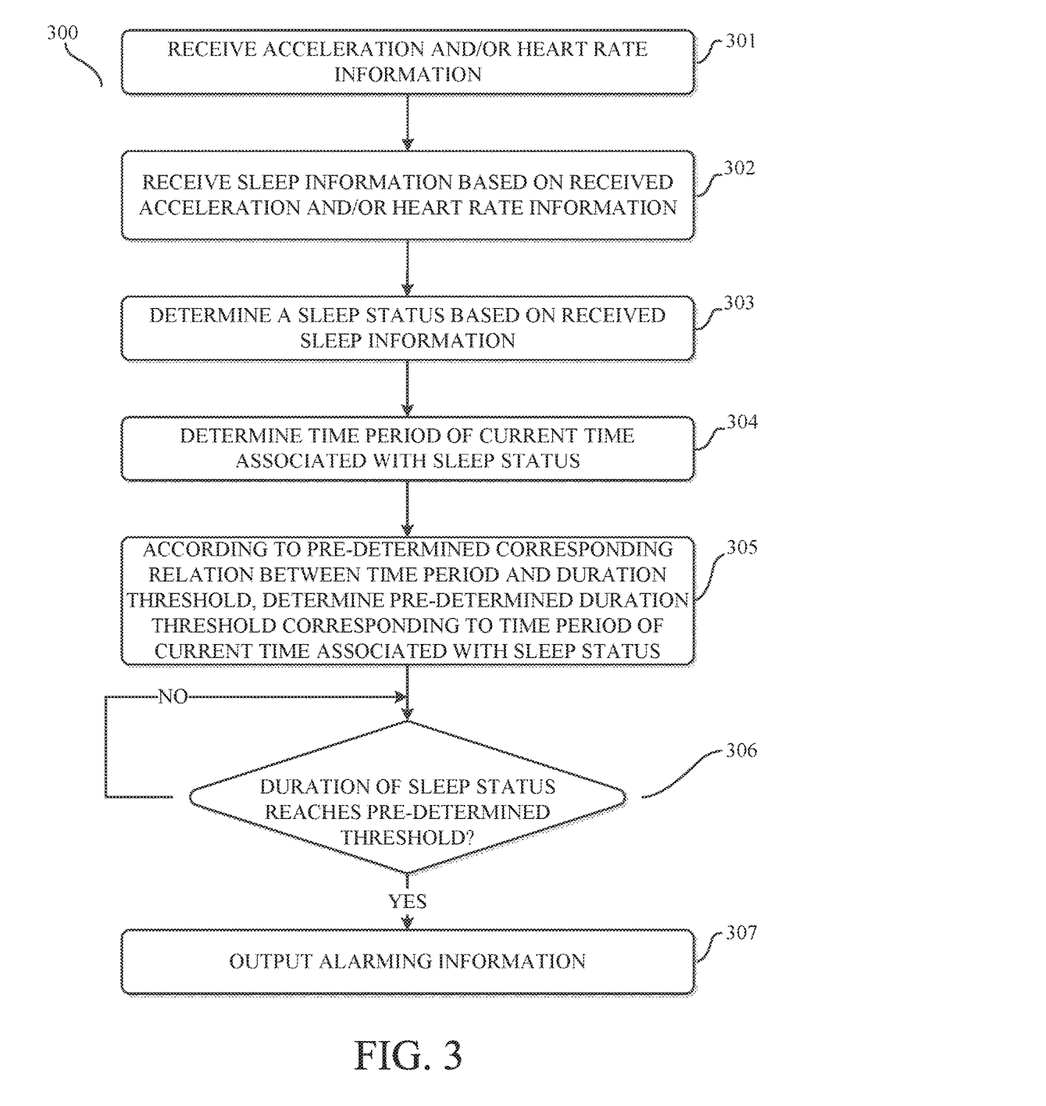
FIG. 3 is a flowchart of a third method for controlling an alarm according to implementations of this disclosure.

FIG. 3 is a flowchart of a third method for controlling an alarm according to implementations of this disclosure. As shown in FIG. 3, this method can be implemented in a wearable device, including the following operations.

When the current date associated with the sleep status is a pre-determined holiday, this implementation can be adopted.

At operation 301, acceleration and/or heart rate information is received.

At operation 302, in accordance with the received acceleration and/or heart rate information, the sleep information is received.

At operation 303, in accordance with the received sleep information, a sleep status is determined.

At operation 304, a time period of a current time associated with the sleep status is determined.

At operation 305, in accordance with a pre-determined corresponding relation between a time period and a duration threshold, a pre-determined duration threshold corresponding to the time period of the current time associated with the sleep status is determined.

At operation 306, it is determined whether duration of the sleep status reaches the pre-determined duration threshold. If the duration of the sleep status reaches the pre-determined duration threshold, the process proceeds to operation 307; otherwise, if the duration of the sleep status does not reach the pre-determined duration threshold, operation 306 is repeated.

At operation 307, alarming information is outputted.

The processes of controlling an alarm are set forth in the above description. In some implementations, the processes can be implemented in a terminal device and an audio playback apparatus. Internal structures and functions of the two devices are set forth in the following description.

Figure 4:
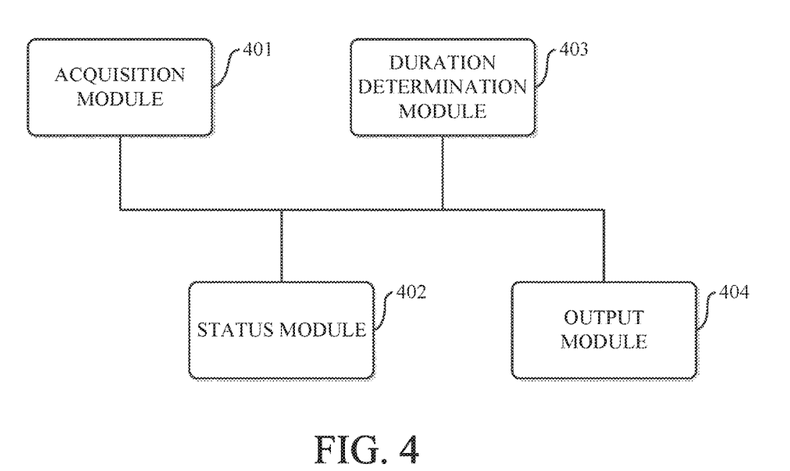
FIG. 4 is a box diagram of an apparatus for controlling volume according to implementations of this disclosure.

FIG. 4 is a box diagram of an apparatus for controlling volume according to implementations of this disclosure. As shown in FIG. 4, the apparatus includes acquisition module 401, status module 402, duration determination module 403 and output module 404.

Acquisition module 401 is used to receive sleep information.

Status module 402 is used to determine a sleep status in accordance with the received sleep information.

Duration determination module 403 is used to determine whether duration of the sleep status reaches a pre-determined duration threshold.

Output module 404 is used to output alarming information if the duration of the sleep status reaches the pre-determined duration threshold.

Figure 5:
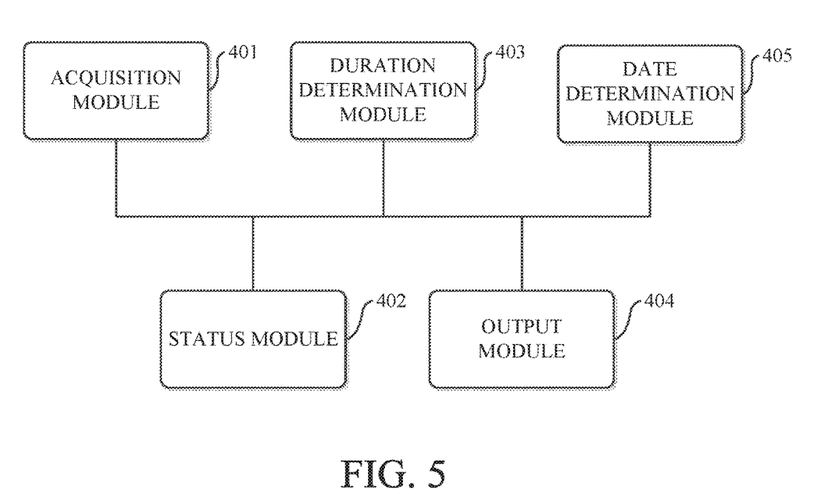
FIG. 5 is a box diagram of another apparatus for controlling volume according to implementations of this disclosure.

As shown in FIG. 5, the abovementioned apparatus further includes date determination module 405.

Date determination module 405 is used to determine whether a current date associated with the sleep status is a pre-determined holiday.

If the current date associated with the sleep status is a pre-determined holiday, and if the duration of the sleep status reaches the pre-determined duration threshold, the aforementioned output module 404 outputs the alarming information.

Figure 6:
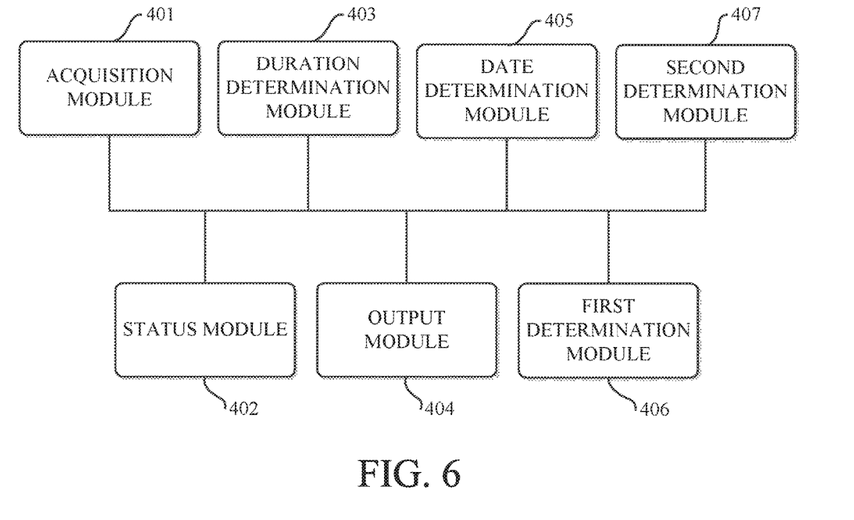
FIG. 6 is a box diagram of a third apparatus for controlling volume according to implementations of this disclosure.

As shown in FIG. 6, the abovementioned apparatus further includes first determination module 406 and second determination module 407.

First determination module 406 is used to determine a time period of a current time associated with the sleep status.

Second determination module 407, in accordance with a pre-determined corresponding relation between a time period and a duration threshold, is used to determine the pre-determined duration threshold corresponding to the time period of the current time associated with the sleep status.

Figure 7:
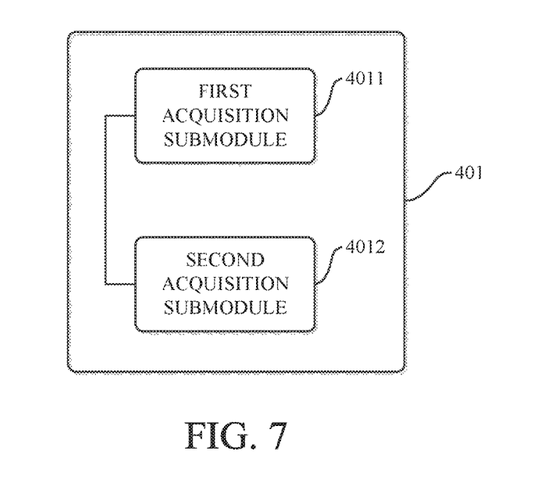
FIG. 7 is a box diagram of an acquisition module according to implementations of this disclosure.

As shown in FIG. 7, the acquisition module 401 includes first acquisition submodule 4011 and second acquisition submodule 4012.

First acquisition submodule 4011 is used to receive acceleration and/or heart rate information.

Second acquisition submodule 4012 is used to receive sleep information in accordance with the received acceleration and/or heart rate information.

Figure 8:
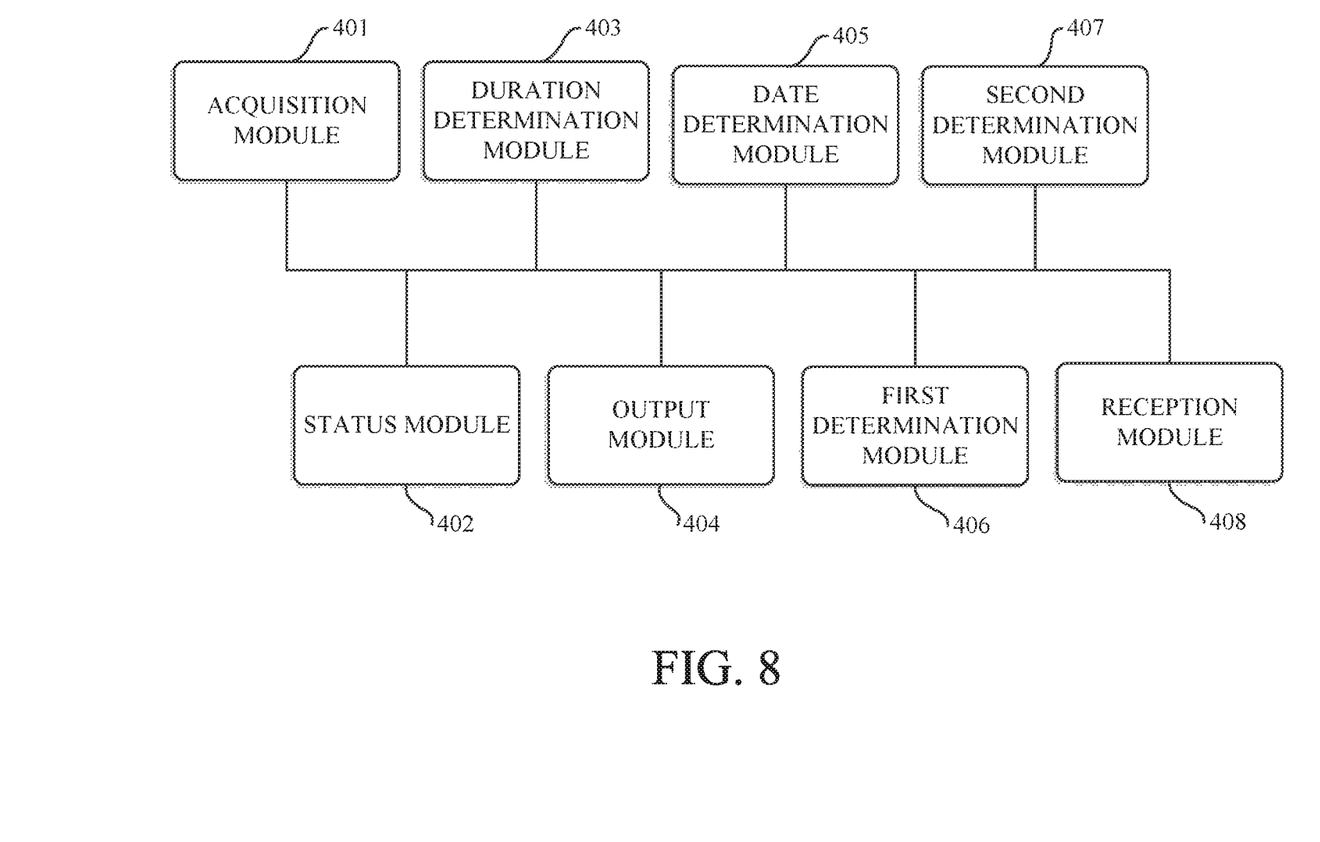
FIG. 8 is a box diagram of a fourth apparatus for controlling volume according to implementations of this disclosure.

As shown in FIG. 8, the aforementioned apparatus further includes reception module 408.

Reception module 408 is used to receive a configuration instruction transmitted from a terminal device, wherein the configuration instruction includes the pre-determined duration threshold.

Technical specialists skilled in the art should understand that, the implementations in this disclosure can be implemented as methods, systems, or computer program products. Therefore, this disclosure can be implemented in forms of a complete hardware implementation, a complete software implementation, and a combination of software and hardware implementation. Further, this disclosure can be embodied as a form of one or more computer program products which are embodied as computer executable program codes in computer writable storage media (including but not limited to disk storage and optical storage).

This disclosure is described in accordance with the methods, devices (systems), and flowcharts and/or block diagrams of computer program products of the implementations, which should be comprehended as each flow and/or block of the flowcharts and/or block diagrams implemented by computer program instructions, and the combinations of flows and/or blocks in the flowcharts and/or block diagrams. The computer program instructions therein can be provided to generic computers, special-purpose computers, embedded computers or other processors of programmable data processing devices to produce a machine, wherein the instructions executed by the computers or the other processors of programmable data processing devices produce an apparatus for implementing the functions designated by one or more flows in the flowcharts and/or one or more blocks in the block diagrams.

The computer program instructions can be also stored in a computer readable storage which is able to boot a computer or other programmable data processing device to a specific work mode, wherein the instructions stored in the computer readable storage produce a manufactured product containing the instruction devices which implements the functions designated by one or more flows in the flowcharts and/or one or more blocks in the block diagrams.

The computer program instructions can also be loaded to a computer or another programmable data processing device to execute a series of operating procedures in the computer or the other programmable data processing device to produce a process implemented by the computer, by which the computer program instructions executed in the computer or the other programmable data processing device provide the operating procedures for the functions designated by one or more flows in the flowcharts and/or one or more blocks in the block diagrams.

Apparently, the technical specialists skilled in the art can perform any variation and/or modification to this disclosure by the principles and within the scope of this disclosure. Therefore, if the variations and modifications herein are within the scope of the claims and other equivalent techniques herein, this disclosure intends to include the variations and modifications thereof.

What is claimed is:

1. A method of controlling an alarm, comprising:
   determining, by a computing device, a sleep status of a user based on sleep information of the user;
   determining, by the computing device, a duration threshold based on a time of day that the user enters a sleep status and pre-determined relationships between the time of day and corresponding duration thresholds, wherein the duration threshold is a first duration threshold at night, the duration threshold is a second duration threshold during daylight hours, and the first duration threshold is longer than the second duration threshold;
   determining, by a timer of the computing device, whether duration of the sleep status reaches the duration threshold, wherein the timer stops when the user is not in the sleep status prior to the duration threshold being reached and resumes when the user returns to the sleep status; and
   based on a determination that the duration of the sleep status reaches the duration threshold, outputting, by the computing device, alarming information for triggering a preset action by the alarm.

2. An apparatus for controlling an alarm, comprising:
   a processor; and
   a memory coupled to the processor, the memory configured to store a set of instructions, which when executed by the processor, become operational with the processor to:
   receive sleep information associated with a user, wherein the sleep information is based on acceleration information or heart rate information;
   determine a sleep status of the user based on the sleep information;
   determine whether a current date associated with the sleep status is one of one or more pre-determined holidays;
   based on a determination that the current date is one of the one or more pre-determined holidays, determine, by a timer, whether duration of the sleep status on the current date reaches a duration threshold, wherein the duration threshold is a first duration threshold when the time is between 22:00-8:00, the duration threshold is a second duration threshold when the time is between 12:00-14:00, and the first duration threshold is longer than the second duration threshold wherein the timer stops when the user is not in the sleep status prior to the duration threshold being reached and resumes when the user returns to the sleep status; and
   based on a determination that the duration of the sleep status on the current date reaches the duration threshold, output alarming information for triggering the alarm on the current date.

3. The apparatus of claim 2, wherein the memory comprises further instructions when executed by the processor become operational with the processor to:
   receive a configuration instruction transmitted from a terminal device.

4. The method of claim 1, wherein determining the sleep status of the user based on the sleep information comprises:
   based on a determination that an activity frequency and an activity amplitude associated with the user are below a first threshold, determining that the user is in the sleep status, wherein the activity frequency and the activity amplitude are determined based on acceleration information; and
   based on a determination that the activity frequency and the activity amplitude associated with the user are above a second threshold, determining that the user is not in the sleep status, wherein the second threshold is greater than or equal to the first threshold.

5. The apparatus of claim 2, wherein the set of instructions operational with the processor to determine the sleep status of the user based on the sleep information comprise further instructions to:
   based on a determination that an activity frequency and an activity amplitude associated with the user are below a first threshold, determine that the user is in the sleep status, wherein the activity frequency and the activity amplitude are determined based on the acceleration information; and
   based on a determination that the activity frequency and the activity amplitude of the user are above a second threshold, determine that the user is not in the sleep status, wherein the second threshold is greater than or equal to the first threshold.

6. The apparatus of claim 2, wherein the set of instructions operational with the processor to determine the sleep status of the user based on the sleep information comprise further instructions to:
   determine whether a match exists between the heart rate information and statistics of pre-determined heart rate information during sleep;
   based on a determination that the match exists, determine that the user is in the sleep status; and
   based on a determination that the match does not exist, determine that the user is not in the sleep status.

7. A system for controlling an alarm, comprising:
   a cell phone, comprising:
      a processor; and
      a memory coupled to the processor, the memory configured to store a set of instructions, which when executed by the processor, become operational with the processor to:
      transmit a configuration instruction; and
   a wearable device, wirelessly connected to the cell phone, comprising:
      a processor; and
      a memory coupled to the processor, the memory configured to store a set of instructions, which when executed by the processor, become operational with the processor to:

receive the configuration instruction from the terminal device, wherein the configuration instruction includes a duration threshold, the duration threshold being a length of time that a user associated with the wearable device is to sleep for;

obtain sleep information of the user associated with the wearable device, wherein the sleep information is based on acceleration information or heart rate information;

determine whether the user associated with the wearable device is asleep based on the sleep information;

determine, by a timer, whether a duration that the user associated with the wearable device has been sleeping reaches the duration threshold, wherein the timer stops when the user is not asleep prior to the duration threshold being reached and resumes when the user has fallen back asleep, wherein the duration threshold is a first duration threshold at night, the duration threshold is a second duration threshold during daylight hours, and the first duration threshold is longer than the second duration threshold; and based on a determination that the duration that the user associated with the wearable device has been sleeping reaches the duration threshold, vibrate to awake the user without disturbing others, wherein the cell phone and the wearable device remain otherwise silent and do not output an audible ring while the wearable device vibrates.

8. The system of claim 7, wherein the set of instructions operational with the processor to determine whether the user associated with the wearable device is asleep based on the sleep information comprise further instructions to:

based on a determination that an activity frequency and an activity amplitude associated with the user are below a first threshold, determine that the user is asleep, wherein the activity frequency and the activity amplitude are determined based on the acceleration information; and based on a determination that the activity frequency and the activity amplitude of the user are above a second threshold, determine that the user is not asleep, wherein the second threshold is greater than or equal to the first threshold.

9. The system of claim 7, wherein the set of instructions operational with the processor to determine whether the user associated with the wearable device is asleep based on the sleep information comprise further instructions to:

determine whether a match exists between the heart rate information of the user associated with the wearable device and pre-determined heart rate information during sleep, wherein the pre-determined heart rate information during sleep is based on statistics;

based on a determination that the match exists, determine that the user is asleep; and based on a determination that the match does not exist, determine that the user is not asleep.

10. The method of claim 1, wherein the first duration threshold is at least double the second duration threshold.

11. The method of claim 1, further comprising:

receiving sleep information associated with the user, wherein the sleep information is based on acceleration information and heart rate information.

12. The method of claim 1, wherein the first duration threshold is at least four times the second duration threshold.

13. The method of claim 1, wherein the first duration threshold is at least double the second duration threshold.

14. The system of claim 7, wherein the timer stops when the user is not in the sleep status prior to the duration threshold being reached and resumes when the user returns to the sleep status.

15. The system of claim 7, wherein the duration threshold is a first duration threshold when the time is between 22:00-8:00, the duration threshold is a second duration threshold when the time is between 12:00-14:00, and the first duration threshold is longer than the second duration threshold.

16. The method of claim 1, wherein the timer stops when the user is not in the sleep status prior to the duration threshold being reached and resumes when the user returns to the sleep status.

17. The method of claim 2, wherein the time stops when the user is not in the sleep status prior to the duration threshold being reached and resumes when the user returns to the sleep status.

18. The method of claim 2, wherein the first duration threshold is at least double the second duration threshold.

19. The method of claim 2, wherein the first duration threshold is at least four times the second duration threshold.

* * * * *